US008961429B2

(12) United States Patent
Ram et al.

(10) Patent No.: US 8,961,429 B2
(45) Date of Patent: Feb. 24, 2015

(54) DEVICE FOR COLLECTION AND PRESERVATION OF TISSUE OR STOOL SAMPLES

(75) Inventors: Jeffrey L. Ram, Huntington Woods, MI (US); Jordan Nechvatal, Stanford, CA (US); Ikuko Kato, Detroit, MI (US)

(73) Assignee: Wayne State University, Detroit, MI (US)

( * ) Notice: Subject to any disclaimer, the term of this patent is extended or adjusted under 35 U.S.C. 154(b) by 930 days.

(21) Appl. No.: 12/733,824

(22) PCT Filed: Sep. 19, 2008

(86) PCT No.: PCT/US2008/010891
§ 371 (c)(1),
(2), (4) Date: Jul. 16, 2010

(87) PCT Pub. No.: WO2009/038763
PCT Pub. Date: Mar. 26, 2009

(65) Prior Publication Data
US 2010/0311165 A1    Dec. 9, 2010

Related U.S. Application Data

(60) Provisional application No. 60/994,436, filed on Sep. 19, 2007.

(51) Int. Cl.
*A61B 10/00*            (2006.01)
(52) U.S. Cl.
CPC ......... *A61B 10/0038* (2013.01); *A61B 10/0096* (2013.01)
USPC ......... 600/562; 600/572; 435/307.1; 435/374

(58) Field of Classification Search
USPC ...................... 600/562–572; 435/307.1, 374
See application file for complete search history.

(56) References Cited

U.S. PATENT DOCUMENTS

| 5,830,154 | A | * | 11/1998 | Goldstein et al. | ............. | 600/572 |
| 5,865,766 | A | | 2/1999 | Bonsall et al. | | |
| 2007/0119508 | A1 | | 5/2007 | West et al. | | |
| 2007/0239067 | A1 | * | 10/2007 | Hibner et al. | ................. | 600/567 |
| 2009/0227893 | A1 | * | 9/2009 | Coonahan et al. | ............ | 600/566 |

OTHER PUBLICATIONS

Product Brochure entitled "Paxgene® Blood RNA," published May 2010, available at www.preanalytix.com.
Product Data Sheet entitled "Oragene® DNA OG-500," PD-BR-017 Issue May 1, 2012, available at www.dnagenotek.com.
Product Data Sheet entitled "Oragene® DNA OG-250," PD-BR-014 Issue Apr. 1, 2012, available at www.dnagenotek.com.

* cited by examiner

*Primary Examiner* — Rene Towa
(74) *Attorney, Agent, or Firm* — Rohm & Monsanto, PLC (57) ABSTRACT

An arrangement for collecting a tissue or stool sample has a sample vial and a source of preservative fluid. A fluid valve controls a flow of the preservative fluid from the source of preservative fluid to the sample vial. An air equalization vent tube is coupled to the source of preservative fluid and an air valve controls a flow of air through the air equalization vent tube, the air valve and the fluid valve being actuated simultaneously. A scoop for collecting the sample is coupled to the sample vial coupler and extends into the sample vial. The preservative fluid flows from the source of preservative fluid to the sample vial by force of gravity upon actuation of the fluid valve. The air equalization vent tube transfers air from the sample vial to the source of preservative fluid upon actuation of the air valve.

19 Claims, 6 Drawing Sheets

DEVICE FOR COLLECTION AND PRESERVATION OF TISSUE OR STOOL SAMPLES

RELATIONSHIP TO OTHER APPLICATION

This application is a US national stage filing under 35 U.S.C. §371 of International Application No. PCT/US2008/010891 filed on Sept. 19, 2008 and claims the benefit under 35 U.S.C. §119(e) of the filing date of U.S. Provisional Patent Application Ser. No. 60/994,436 filed Sep. 19, 2007, Conf. No. 7514 (Foreign Filing License Granted), in the names of the same inventors as herein. The disclosure in the identified U.S. Provisional Patent Application is incorporated herein by reference.

BACKGROUND OF THE INVENTION

1. Field of the Invention

This invention relates generally to systems for collecting and preserving tissue samples, and more particularly, to a system that enables small pieces of human tissue or stool samples to be rapidly immersed and preserved at room temperature in toxic preservatives, for later molecular and structural analysis, without danger for the user of exposure to the toxic preservatives.

2. Description of the Prior Art

Preservation of human tissues and stool samples for molecular and structural analysis frequently requires rapid immersion of samples in highly toxic preservatives, some of which produce volatile fumes that are dangerous to breathe, according to accompanying material data safety sheets. There is a need for a system that allows introduction of the sample into a storage container or sample chamber that is sealed off from the preservative, and that enables rapid movement of the preservative into the sample chamber after the chamber has been sealed.

Several devices exist for collecting fluid samples and preserving their RNA and DNA by immediate treatment with toxic volatile preservatives. These known devices include, for example:

(a) Paxgene™ Blood RNA System—This is a PreAnalytix/BD Vacutainer™ product for preserving RNA in blood. The device is operated like an ordinary Vacutainer™ blood sample collection arrangement except that the tube contains a proprietary preservative called PAXgene. In this arrangement, blood is collected during venipuncture and is sucked into the tube, without exposure of the user to its contents, upon the piercing of the Vacutainer™ plug with the phlebotomy needle. PAXgene™ tubes are an approved medical device for the purpose of collecting and preserving blood RNA. However, the utility of this known arrangement is limited to the collection of fluid samples, and is not useful in the collection of solid samples, such as stool samples.

(b) Oragene™DNA Self-Collection Kit—DNA from Saliva from DNA Genotek

In this known arrangement, a volatile toxic chemical preservative is contained under an internal disk. A saliva sample is inserted on top of the disk. When the top of the device is screwed all the way down, the disk is rotated, allowing access of the preservative to the saliva with which it mixes. The known Oragene DNA Self-Collection Kit constitutes a way to collect and preserve large amounts of DNA from saliva. One feature of this known arrangement is that saliva samples do not require special handling or storage because the DNA in Oragene is stable for years at room temperature. However, the utility of this known arrangement is limited to the collection of fluid samples, and is not useful in the collection of solid samples, such as stool samples.

(c) Oragene devices: Disk device and Tube device: The disk in this known arrangement prevents a stool or tissue sample from becoming fully immersed in the preservative fluid. Both disk and tube device: The total volume of the preservative is less than 2 ml. This is too small of a volume of preservative for the amounts of stool or tissue typically collected, which need to be preserved in at least 5 ml of preservative each. There is no mechanism that assures that if the sample is tissue or stool (rather than liquid, which the device was designed for) that it would stay fully immersed in the preservative since the preservative can run back into the source chamber of the preservative, leaving the tissue/stool sample behind.

Even if the Oragene tube device is modified to accommodate a larger volume, such as 7.5 ml, the system falls short of achieving the desired goals. More specifically, with larger volumes, the fluid fills the lower chamber (which is only 5 mL in volume) so high that fluid leakage out the threads occurs as the top section is being screwed in. Nevertheless, a volume of 7.5 ml would be necessary to assure complete immersion of the sample regardless of the orientation of the device.

This problem is exacerbated by the fact that there is no "pressure relief" mechanism, so that as the upper part is screwed in, the pressure inside the device increases as the top is screwed in further to make the final cutting of the inner membrane and seal. In fact, when fully closed, the Oragene tube device has a larger positive pressure that might promote leakage of the contents if damaged or inadequately sealed.

There is a need, therefore, for a system for collecting solid tissue samples, such as stool samples, that can accommodate a relatively large volume of preservative fluid.

There is additionally a need for a system for collecting solid tissue samples, such as stool samples, that can accommodate a relatively large volume of preservative fluid and that does not leak, particularly when the system is pressurized.

There is a further need for a system for collecting individual solid tissue bio-samples.

There is a still further need for a system for collecting individual solid tissue bio-samples that can easily be used by relatively unskilled individuals for effecting self collection.

SUMMARY OF THE INVENTION

The aforementioned deficiencies in the prior art are satisfied by an apparatus for collecting a tissue sample. In accordance with the present invention, there is provided a sample vial for receiving the tissue sample and a source of preservative fluid. A fluid valve controls a flow of the preservative fluid from the source of preservative fluid to the sample vial. An air equalization vent tube is coupled to the source of preservative fluid and an air valve controls a flow of air through the air equalization vent tube.

In one embodiment, there are further provided a fluid valve actuator for controlling the fluid valve and an air valve actuator for controlling the air valve. A valve actuator coupler couples the fluid valve actuator and the air valve actuator for actuating the fluid valve and the air valve simultaneously.

In a further embodiment, a sample vial coupler serves to removably attach the sample vial to the fluid valve and the air valve. A collection scoop is used for collecting the tissue sample, and in some embodiments the collection scoop is coupled to the sample vial coupler and arranged to extend into the sample vial when the sample vial is coupled to the fluid valve and the air valve.

In a gravity feed embodiment of the invention, the source of preservative fluid is disposed spatially superior to the sample vial whereby the preservative fluid flows from the source of preservative fluid to the sample vial by force of gravity upon actuation of the fluid valve. The air equalization vent tube is configured to transfer air from the sample vial to the source of preservative fluid upon actuation of the air valve. In a highly advantageous embodiment, the air equalization vent tube is configured to transfer air from the sample vial to the source of preservative fluid upon actuation of the fluid valve.

In accordance with a method aspect of the invention, there are provided the steps of:

depositing the tissue sample into a collection vial;

attaching the collection vial sealingly to a valve arrangement;

operating a fluid valve arrangement to permit a preservative fluid to flow from a source of preservative fluid into the collection vial; and operating an air valve arrangement to permit air in the collection vial to flow into the source of preservative fluid.

In one embodiment of this method aspect of the invention, the steps of operating a fluid valve arrangement and operating an air valve arrangement are performed simultaneously.

In a further embodiment, there are provided the further steps of:

further operating the fluid valve arrangement to isolate the collection vial and the preservative fluid therein from the source of preservation fluid; and further operating the air valve arrangement to isolate the collection vial and the preservative fluid therein from the source of preservation fluid.

The steps of further operating the fluid valve arrangement and further operating the air valve arrangement are performed simultaneously in some embodiments.

In accordance with a further apparatus aspect of the invention, there is provided a sample vial for receiving the tissue sample and a source of preservative fluid. A fluid valve controls a flow of the preservative fluid from the source of preservative fluid to the sample vial and a fluid valve actuator controls the fluid valve. An air equalization vent tube is coupled to the source of preservative fluid and an air valve controls a flow of air through the air equalization vent tube. Additionally, an air valve actuator controls the air valve and a valve actuator coupler couples the fluid valve actuator and the air valve actuator for actuating the fluid valve and the air valve simultaneously.

In one embodiment of this further apparatus aspect of the invention there is further provided a collection scoop for collecting the tissue sample. The collection scoop is, in some embodiments, coupled to the sample vial coupler and arranged to extend into the sample vial when the sample vial is coupled to the fluid valve and the air valve.

In a gravity feed embodiment of this further apparatus aspect of the invention, the source of preservative fluid is disposed spatially superior to the sample vial whereby the preservative fluid flows from the source of preservative fluid to the sample vial by force of gravity upon actuation of the fluid valve. The air equalization vent tube is configured to transfer air from the sample vial to the source of preservative fluid upon actuation of the air valve. In a highly advantageous embodiment, the air equalization vent tube is configured to transfer air from the sample vial to the source of preservative fluid upon actuation of the fluid valve.

BRIEF DESCRIPTION OF THE DRAWING

Comprehension of the invention is facilitated by reading the following detailed description, in conjunction with the annexed drawing, in which.

DETAILED DESCRIPTION

Figure 1:
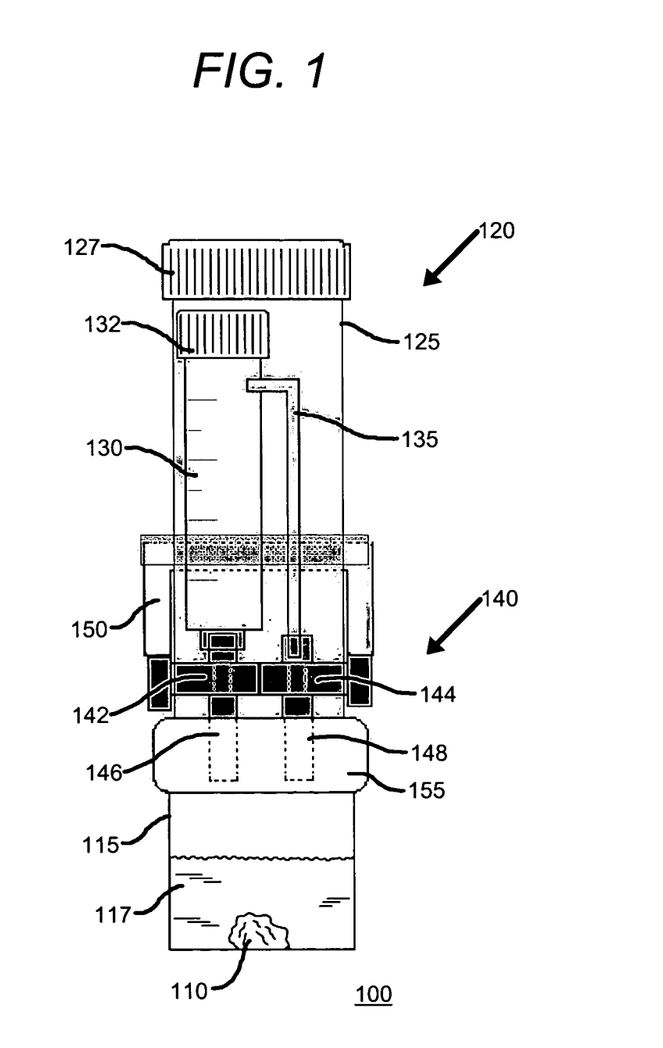
FIG. 1 is a simplified schematic representation of a collection system constructed in accordance with the invention and shown after a tissue or stool sample has been collected.

FIG. 1 is a simplified schematic representation of a specific illustrative embodiment of a collection system 100 constructed in accordance with the invention and shown after a tissue or stool sample 110 has been collected. As shown in this figure, tissue or stool sample 110 has been deposited in a collection vial 115 and is shown to be submerged in a preservative fluid 117. In a typical application for the present invention, the preservative fluid is toxic and it is important that the user of the system (not shown) not come into contact with, or breath the fumes of, the preservative fluid.

An upper portion 120 of collection system 100 if formed, in this specific illustrative embodiment of the invention, of an outer container 125 that is closed at it upper end with a cap 127. Contained within outer container 125 is an inner container 130 that is closed at its respective upper end with a cap 132. As will be discussed below, inner container 130 is used to contain the toxic preservative fluid 117 before it is poured into collection vial 115. There is additionally shown in this figure an air pressure equalization tube 135 that, as will be described below, serves to facilitate the transfer of the preservative fluid 117 from inner container 130 to collection vial 115.

Intermediate of collection vial 115 and upper portion 120 of collection system 100 is a dual valve arrangement 140. As shown, valve arrangement 140 has a first valve 142 that couples inner container 130 to a port 146. Similarly, a second valve 144 couples equalization tube 135 to a port 148. Valves 142 and 144, in this specific illustrative embodiment of the invention, are operated simultaneously by actuation of a valve handle 150 that is coupled to both valves. As such, the valves function as a controlled manifold.

Ports 146 and 148 in this embodiment are contained within a coupler 155 that joins collection vial 115 to valve arrangement 140. As shown, the ports are directed toward the interior of collection vial 115.

Figure 2:
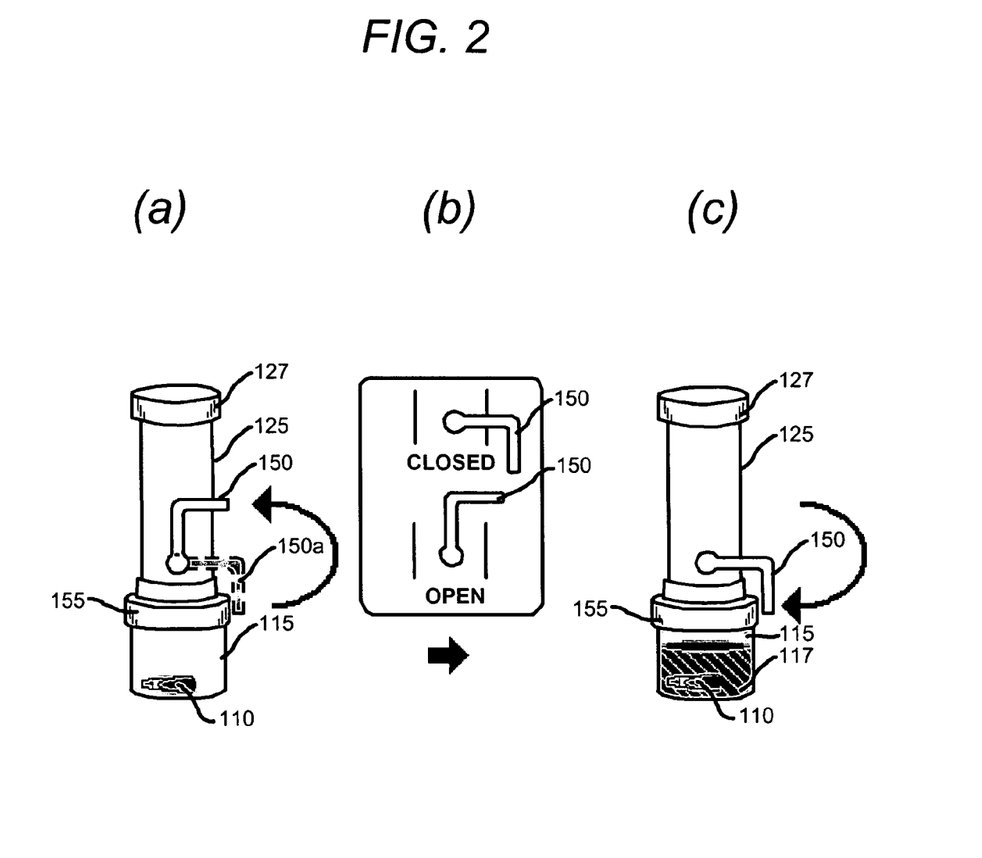
FIGS. 2(a), 2(b), and 2(c) are simplified schematic representations of a specific illustrative embodiment of the invention and show the sequence of operation of the present collection system.

FIGS. 2(a), 2(b), and 2(c) are simplified schematic representations of a specific illustrative embodiment of the invention, and serve to illustrate the sequence of operation of the present collection system. Elements of structure that have previously been discussed are similarly designated. As shown in FIG. 2(a), collection system 100 has been provided with tissue or stool sample 110 that is contained within collection vial 115. While in the condition represented in FIG. 2(a), preservative fluid 117 (not shown in this figure) is contained within inner container 130 (not shown in this figure).

As shown in FIG. 2(c), upon actuation of valve handle 150 to the position represented by the dashed line (150a) of FIG. 2(a), preservative fluid 117 is fed by operation of gravity from inner container 130 (not shown in this figure) to collection vial 115. FIG. 2(c) illustrates the condition of the system after valve handle 150 has been actuated. This FIG. 2(c)) shows tissue or stool sample 110 submerged in preservative fluid 117.

FIG. 2(b) illustrates the relative positions of valve handle 150 of the present specific illustrative embodiment of the invention in respective closed and open states.

Figure 3:
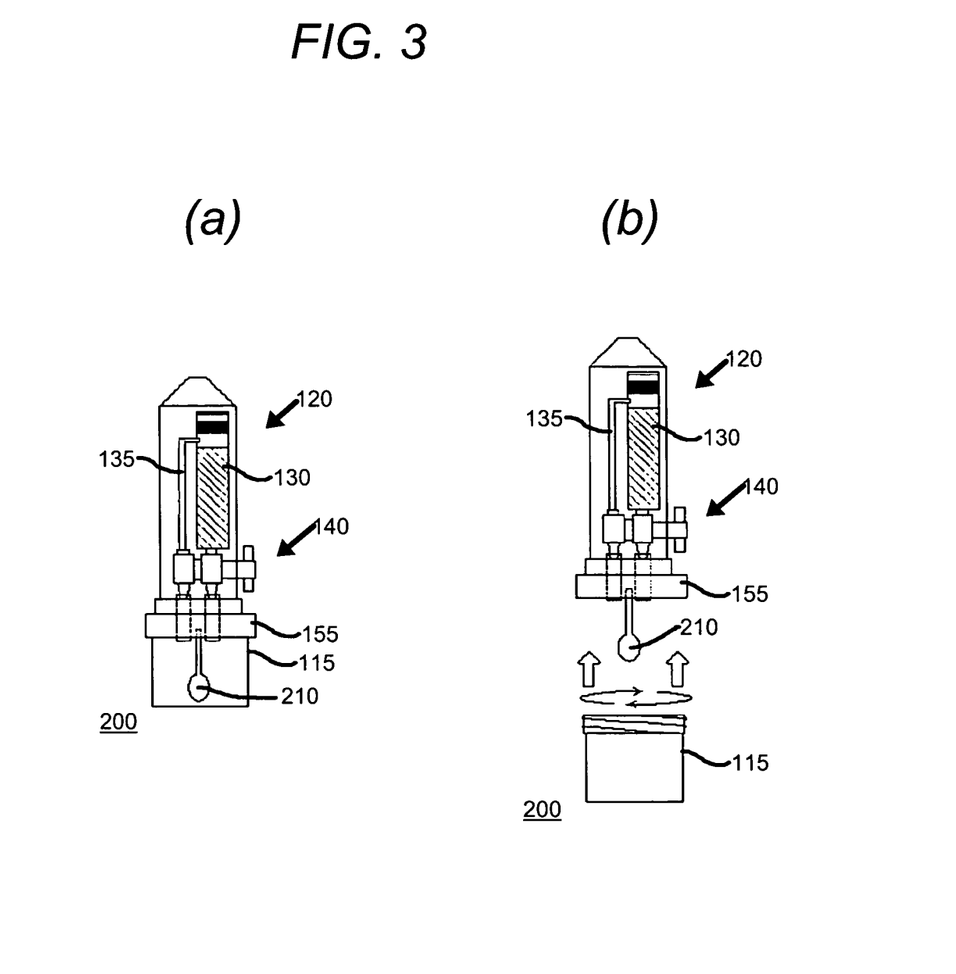
FIGS. 3(a) and 3(b) are simplified schematic representations of a specific illustrative embodiment of the invention having a collection spoon formed therewith.

FIGS. 3(a) and 3(b) are simplified schematic representations of a specific illustrative embodiment of the invention in the form of collection system 200 having a collection spoon 210 formed therewith. Elements of structure that have previously been discussed are similarly designated. In operation of this specific illustrative embodiment of the invention, collection vial 115 is removed by rotating same to unscrew it from coupler 155. The exposed collection spoon 210 is then used to scoop a sample of tissue or stool (not shown in this figure), and the collection vial then is reattached to coupler 155 as indicated in FIG. 3(b).

Figure 4:
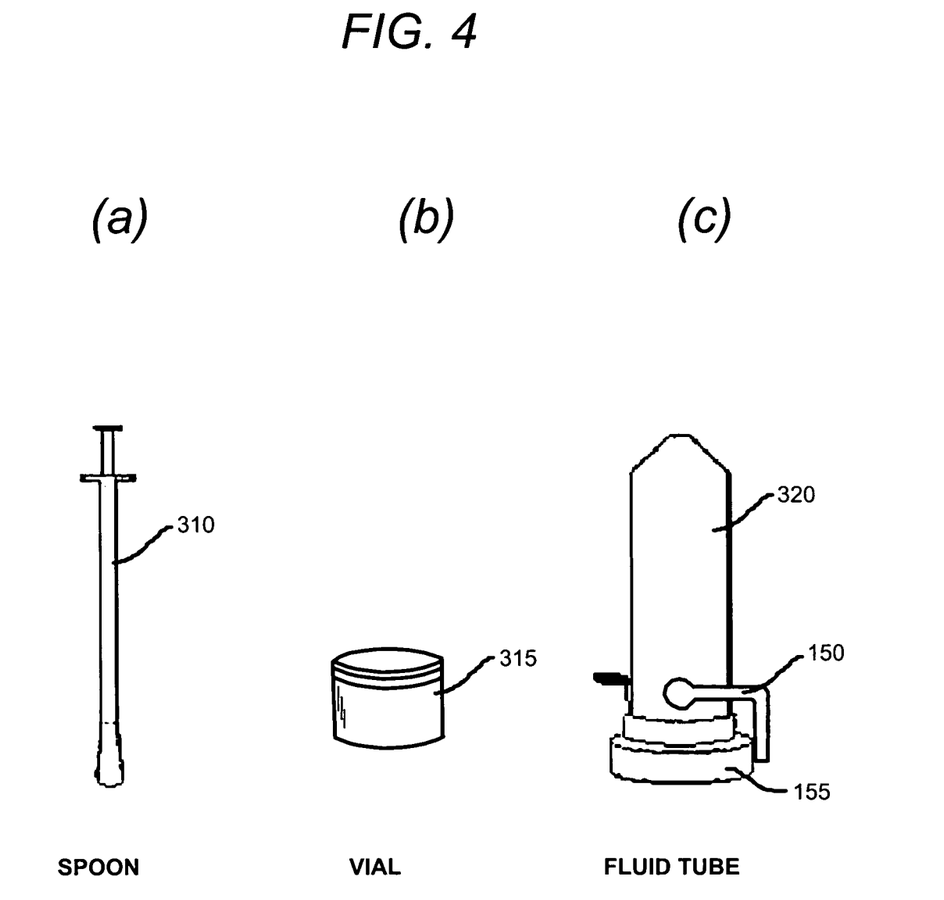
FIGS. 4(a), 4(b), and 4(c) are simplified schematic representations of a collection spoon, a collection vial, and fluid tube components, respectively, of a specific illustrative embodiment of the invention.

FIGS. 4(a), 4(b), and 4(c) are simplified schematic representations of a collection spoon 310, a collection vial 315, and a fluid tube 320, respectively, all of which are components of a tissue or stool sample collection kit in accordance with a collection kit aspect of the invention. Elements of structure that have previously been discussed are similarly designated. The operation of collection spoon 310 is illustrated below in relation to FIG. 5.

Figure 5:
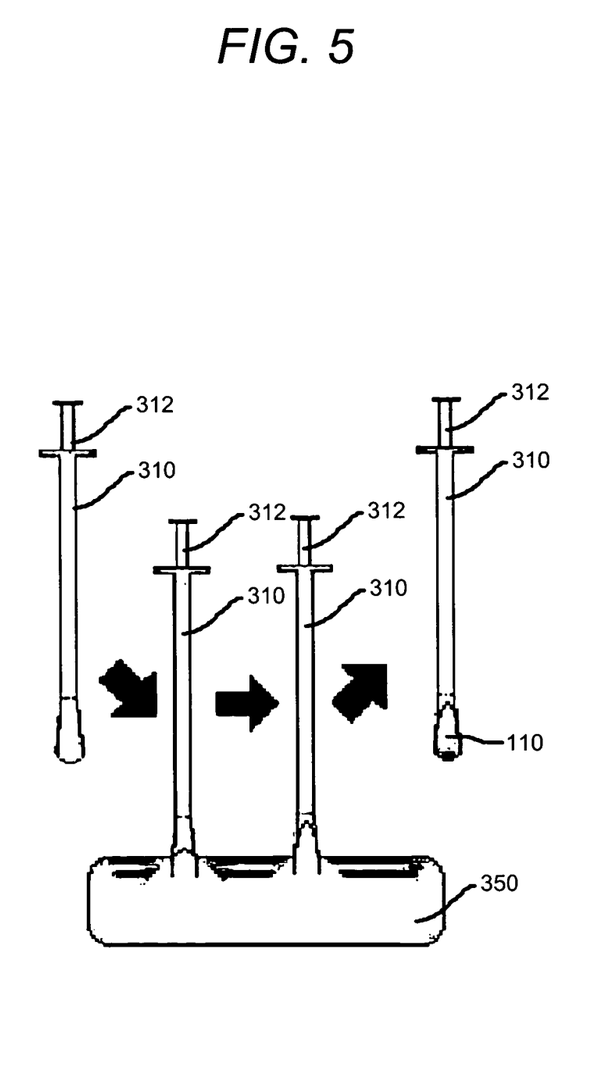
FIG. 5 is a simplified schematic representation of a collection spoon being used to collect a tissue or stool sample.

FIG. 5 is a simplified schematic representation of collection spoon 310 that is depicted as being used to collect a tissue or stool sample 110. Elements of structure that have previously been discussed are similarly designated. As shown in this figure, collection spoon 310 is inserted into a source 350 of tissue or stool. A plunger portion 312, which may in certain embodiments of the invention be spring-loaded (not shown), is actuated to cause a portion of the tissue or stool 350 desired to be sampled to be drawn part way into the shaft (not specifically designated) of collection spoon 310. Thereafter, collection spoon 310 is placed over collection vial 115 as shown in FIG. 6.

Figure 6:
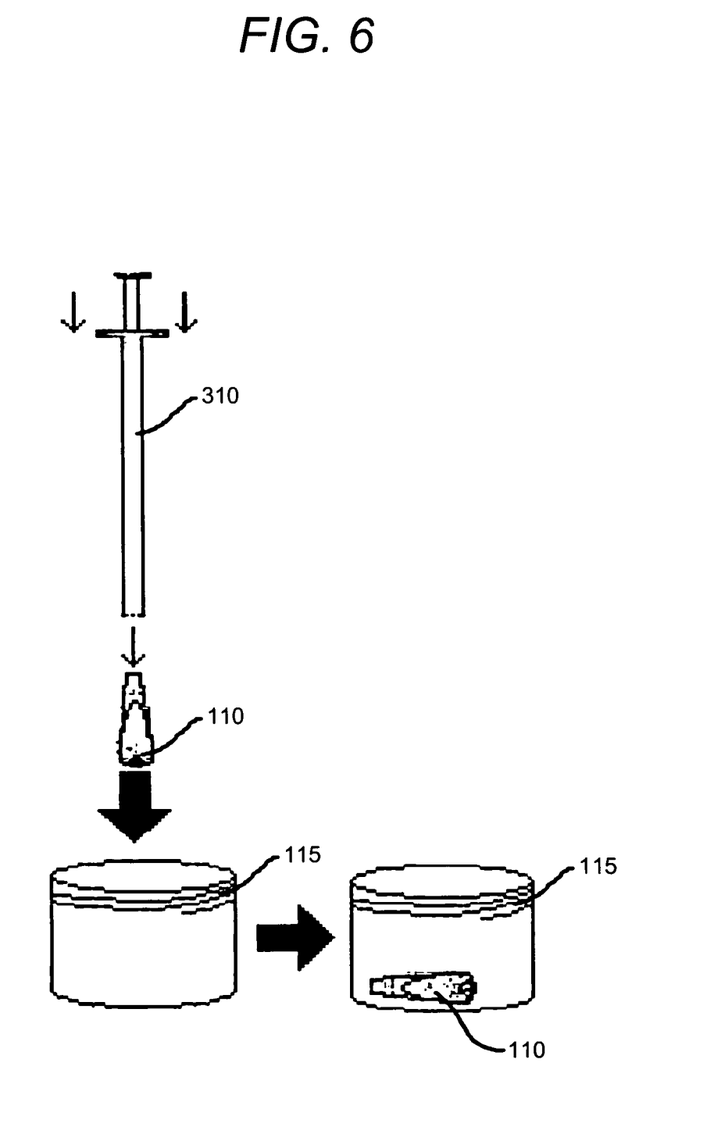
FIG. 6 is a simplified schematic representation of the collection spoon of FIG. 5 being used to deposit the tissue or stool sample into a collection vial.

FIG. 6 is a simplified schematic representation of collection spoon 310 of FIGS. 4(a) and 5 being used to deposit the tissue or stool sample 110 into a collection vial 115. More specifically, collection spoon 310 is placed over collection vial 115 and plunger portion 312 is actuated to deposit tissue or stool sample 110 into collection vial 115. Collection vial 115 is then coupled to coupler 155 before toxic preservative fluid 117 is released. Thus, the user (not shown) is never exposed to preservative fluid 117 or its fumes.

Although the invention has been described in terms of specific embodiments and applications, persons skilled in the art may, in light of this teaching, generate additional embodiments without exceeding the scope or departing from the spirit of the invention described and claimed herein. Accordingly, it is to be understood that the drawing and description in this disclosure are proffered to facilitate comprehension of the invention, and should not be construed to limit the scope thereof.

What is claimed is:

1. Apparatus for collecting a tissue sample, the apparatus comprising:
    a sample vial for receiving the tissue sample;
    a source of preservative fluid;
    a fluid valve for controlling a flow of the preservative fluid from said source of preservative fluid into said sample vial such that said preservative fluid contacts said tissue sample;
    an air equalization vent tube coupled to said sample vial and to said source of preservative fluid; and
    an air valve for controlling a flow of air through said air equalization vent tube from said sample vial into said source of preservative fluid to equalize the pressure in said source of preservative fluid and said sample vial in response to the flow of preservative fluid from said source of preservative fluid into said sample vial to facilitate transfer of the preservative fluid into said sample vial.

2. The apparatus of claim 1, wherein there are further provided:
    a fluid valve actuator for controlling said fluid valve; and
    an air valve actuator for controlling said air valve.

3. The apparatus of claim 2, wherein there is further provided a valve actuator coupler for coupling said fluid valve actuator and said air valve actuator for actuating said fluid valve and said air valve simultaneously.

4. The apparatus of claim 1, wherein there is further provided a sample vial coupler for removably attaching said sample vial to said fluid valve and said air valve.

5. The apparatus of claim 4, wherein there is further provided a collection scoop for collecting the tissue sample.

6. The apparatus of claim 5, wherein said collection scoop is coupled to said sample vial coupler and arranged to extend into said sample vial when said sample vial is coupled to said fluid valve and said air valve.

7. The apparatus of claim 1, wherein said source of preservative fluid is disposed spatially superior to said sample vial whereby the preservative fluid flows from said source of preservative fluid to said sample vial by force of gravity upon actuation of said fluid valve.

8. The apparatus of claim 1, wherein said air equalization vent tube is configured to transfer air from said sample vial to said source of preservative fluid upon actuation of said air valve.

9. The apparatus of claim 8, wherein said air equalization vent tube is configured to transfer air from said sample vial to said source of preservative fluid upon actuation of said fluid valve.

10. The apparatus of claim 1, wherein there is further provided a collection scoop for collecting the tissue sample.

11. A method of collecting a tissue sample, the method comprising the steps of:
    depositing the tissue sample into a collection vial;
    attaching the collection vial sealingly to a valve arrangement;
    operating a fluid valve arrangement to permit a preservative fluid to flow from a source of preservative fluid into the collection vial; and
    operating an air valve arrangement to permit air in the collection vial to flow into the source of preservative fluid, whereby the air pressure in the collection vial and in the source of preservative fluid are equalized as the preservative fluid flows from the source of preservative fluid to the collection vial.

12. The method of claim 11, wherein said steps of operating a fluid valve arrangement and operating an air valve arrangement are performed simultaneously.

13. The method of claim 11, wherein there are further provided the steps of:
further operating the fluid valve arrangement to isolate the collection vial and the preservative fluid therein from the source of preservation fluid; and
further operating the air valve arrangement to isolate the collection vial and the preservative fluid therein from the source of preservation fluid.

14. The method of claim 13, wherein said steps of further operating the fluid valve arrangement and further operating the air valve arrangement are performed simultaneously.

15. Apparatus for collecting a tissue sample, the apparatus comprising:
a sample vial for receiving the tissue sample;
a source of preservative fluid;
a fluid valve for controlling a flow of the preservative fluid from said source of preservative fluid to said sample vial;
a fluid valve actuator for controlling said fluid valve;
an air equalization vent tube coupled to said source of preservative fluid and to said sample vial;
an air valve for controlling a flow of air through said air equalization vent tube as the preservative fluid flows from the source of preservative fluid to said sample vial;
an air valve actuator for controlling said air valve; and
a valve actuator coupler for coupling said fluid valve actuator and said air valve actuator for actuating said fluid valve and said air valve simultaneously.

16. The apparatus of claim 15, wherein there is further provided a collection scoop for collecting the tissue sample.

17. The apparatus of claim 16, wherein said collection scoop is coupled to said sample vial coupler and arranged to extend into said sample vial when said sample vial is coupled to said fluid valve and said air valve.

18. The apparatus of claim 15, wherein said source of preservative fluid is disposed spatially superior to said sample vial whereby the preservative fluid flows from said source of preservative fluid to said sample vial by force of gravity upon actuation of said fluid valve.

19. The apparatus of claim 15, wherein said air equalization vent tube is configured to transfer air from said sample vial to said source of preservative fluid upon actuation of said air valve and said fluid valve.

* * * * *